(12) United States Patent
Bosch et al.

(10) Patent No.: US 6,573,389 B1
(45) Date of Patent: Jun. 3, 2003

(54) BIDENTATE ORGANOPHOSPHOROUS LIGANDS AND THEIR USE

(75) Inventors: Boris E. Bosch, Cologne (DE); Harald Trauthwein, Munich (DE); Thomas Riermeier, Floersheim (DE); Uwe Dingerdissen, Jugenheim (DE); Axel Monsees, Frankfurt (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/926,380

(22) PCT Filed: Apr. 13, 2000

(86) PCT No.: PCT/EP00/03303

§ 371 (c)(1),
(2), (4) Date: Dec. 6, 2001

(87) PCT Pub. No.: WO00/64914

PCT Pub. Date: Nov. 2, 2000

(30) Foreign Application Priority Data

Apr. 23, 1999 (DE) .......................................... 199 18 420

(51) Int. Cl.$^7$ .......................................... C07D 333/00
(52) U.S. Cl. .......................................................... 549/6
(58) Field of Search .............................................. 549/6

(56) References Cited

U.S. PATENT DOCUMENTS

| | | | |
|---|---|---|---|
| 4,595,753 A | | 6/1986 | Oswald et al. |
| 6,077,958 A | * | 6/2000 | Antognazza et al. ......... 548/101 |
| 6,153,758 A | * | 11/2000 | Sannicolo et al. .......... 548/111 |
| 6,162,929 A | * | 12/2000 | Foricher et al. ............... 549/6 |
| 6,339,161 B1 | * | 1/2002 | Xu et al. ....................... 549/3 |
| 6,472,533 B1 | * | 10/2002 | Burgess ...................... 548/119 |
| 6,472,539 B1 | * | 10/2002 | Yokozawa et al. .......... 549/220 |

FOREIGN PATENT DOCUMENTS

EP   0 614 901   9/1994

OTHER PUBLICATIONS

E. Shirakawa, et al., Tetrahedron Letters, vol. 38, No. 21, pp. 3759–3762, "An Iminophosphine–Palladium Catalyst for Cross–Coupling of Aryl Halides with Organostannanes", May 26, 1997.

K. Kamikawa, et al., Journal of Organic Chemistry, vol. 63, No. 23, pp. 8407–8410, "Palladium–Catalyzed Amination of Aryl Bromides Utilizing Arene–Chromium Complexes as Ligands", Nov. 13, 1998.

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

The present invention relates to unsymmetric bidendate organophosphorus ligands of the formula (I) which have a modular structure and have a trivalent phosphine function and a second trivalent phosphorus group which is bound via a heteroatom to a chiral ligand framework, $$R^1R^2PZC^*HR^3XP(YR^4)(YR^5) \tag{I}$$

where

X is —O—, —S— or —NR$^6$—,

Y is a direct phosphorus-carbon bond, —O— or —NR$^7$—,

Z represents 1 to 6 carbon atoms which are joined by single or double bonds and link the phosphine unit PR$^1$R$^2$ to the carbon center C*, and P is trivalent phosphorus.

The invention also relates to complexes comprising such a chiral ligand system of the formula (I).

32 Claims, No Drawings

BIDENTATE ORGANOPHOSPHOROUS LIGANDS AND THEIR USE

This Appln is a 371 of PCT/EP00/03303 Apr. 13, 2000.

DESCRIPTION

Trisubstituted organophosphorus compounds are of great importance as ligands in homogeneous catalysis. Variation of the substituents on the phosphorus in such compounds enables the electronic and steric properties of the phosphorus ligand to be influenced in a targeted way, so that selectivity and activity in homogeneously catalyzed processes can be controlled. Enantiomerically enriched chiral ligands are used in asymmetric synthesis and asymmetric catalysis, and in this case it is important that the electronic properties and the stereochemical properties of the ligand are optimally matched to the respective catalysis problem. There is therefore a great need for chiral ligands which differ stereochemically and/or electronically in order to discover ligands which have been optimally "tailored" to a particular asymmetric catalytic reaction. In the ideal case, it is therefore desirable to have a chiral ligand framework which can be modified in a wide variety of ways and can be varied within a wide range in respect of its steric and electronic properties.

The structural variety of the phosphorus ligands known hitherto is very wide. These ligands can be classified, for example, according to classes of compounds, and examples of such classes of compounds are trialkylphosphines and triarylphosphines, phosphites, phosphinites, phosphonites, aminophosphines, etc. This classification according to classes of compounds is particularly useful for describing the electronic properties of the ligands.

Alternatively, phosphorus ligands can be classified according to their symmetry properties or according to the "denticity" of the ligands. This structuring takes account, in particular, of the stability, activity and (potential) stereoselectivity of metal complexes with phosphorus ligands as catalyst precursors/catalysts. Apart from the widespread $C_2$-symmetric bidentate ligand systems such as DUPHOS, DIOP, BINAP or DEGUPHOS, unsymmetrical bidentate organophosphorus ligands are becoming increasingly significant in asymmetric catalysis. Important examples are the large class of versatile chiral ferrocenylphosphine ligands such as JOSIPHOS, for example, the aminophosphine-phosphinite ligands such as PINDOPHOS or DPAMPP which are used particularly successfully in the asymmetric hydrogenation of olefins, or phosphine-phosphite ligands such as BINAPHOS or BIPHEMPHOS, which represent milestones in the asymmetric hydroformylation of olefins. An important aspect of the success of these classes of compounds is ascribed to the creation of a particularly asymmetric environment of the metal center by means of these ligand systems. To utilize such an environment for effective transfer of the chirality, it is advantageous to control the flexibility of the ligand system as inherent limitation of the asymmetric induction.

The present invention describes novel, unsymmetrical, bidentate and chiral phosphorus ligand systems which in a unique way combine the above-described important features for effective asymmetric induction. They create both a highly asymmetric coordination sphere with organophosphorus donors which can be modified independently of one another, and they can be modified simply over an extraordinarily wide range in terms of their steric and electronic properties. Furthermore, they allow gradual adjustment of the rigidity by means of a change in the basic structure of the "ligand backbone". At the same time, in contrast to many established ligand systems, the compounds of the invention can be obtained via simple syntheses over a wide range of variations.

The present invention relates to unsymmetric bidendate organophosphorus ligands of the formula (I) which have a modular structure and have a trivalent phosphine function and a second trivalent phosphorus group which is bound via a heteroatom to a chiral ligand framework, $$R^1R^2PZC^*HR^3XP(YR^4)(YR^5) \qquad (I)$$

where $R^1$–$R^5$ are identical or different and are each a hydrogen atom or a $C_1$–$C_{50}$ group such as $C_1$–$C_{24}$-alkyl, $C_2$–$C_{24}$-alkenyl, $C_3$–$C_8$-cycloalkyl, $C_3$–$C_8$-cycloalkenyl, $C_6$–$C_{14}$-aryl, phenyl, naphthyl, fluorenyl, $C_2$–$C_{13}$-heteroaryl in which the number of heteroatoms, in particular from the group consisting of N, O, S, can be 1–4, where the cyclic aliphatic or aromatic radicals are preferably 5- to 7-membered rings and the specified substituents can each bear one or more substituents selected independently from the group consisting of hydrogen, $C_1$–$C_{20}$-alkyl, $C_2$–$C_{20}$-alkenyl, $C_1$–$C_{10}$-haloalkyl, $C_3$–$C_8$-cyclo-alkyl, $C_3$–$C_8$-cycloalkenyl, $C_2$–$C_8$-heteroalkyl, $C_1$–$C_9$-heteroalkenyl, $C_6$–$C_{14}$-aryl, phenyl, naphthyl, fluorenyl, $C_2$–$C_7$-heteroaryl in which the number of heteroatoms, in particular from the group consisting of N, O, S, can be 1–4, $C_1$–$C_{10}$-alkoxy, $C_1$–$C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1$–$C_8$-substituted amino of the forms mono-, di-, tri-$C_1$–$C_8$-alkylamino or $C_2$–$C_8$-alkenylamino or mono-, di-, tri- $C_6$–$C_8$-arylamino or $C_1$–$C_8$-alkyl-$C_6$–$C_8$-arylamino, cyano, carboxyl, carboxylato of the formula $COOR^8$, where $R^8$ is a monovalent cation or a $C_1$–$C_8$-alkyl group, $C_1$–$C_8$-acyloxy, sulfinato, sulfonato of the formula $SO_3R^8$, phosphato of the formula $PO_3H_2$, $PO_3HR^8$, $PO_3R^8{}_2$, tri-$C_1$–$C_6$-alkylsilyl, and where two of the substituents can also be bridged and $R^1$ and $R^2$ or $R^4$ and $R^5$ can be joined to one another so as to form a 4–8-membered cyclic compound, X is —O—, —S— or —$NR^5$—, $R^6$ is a radical as defined for $R^1$–$R^5$, Y is a direct phosphorus-carbon bond, —O— or —$NR^7$—, where $R^7$ is a radical as defined for $R^1$–$R^5$, Z represents one to six carbon atoms which are joined by single or double bonds and link the phosphine unit $PR^1R^2$ to the carbon center C*, where Z is part of an aliphatic, cycloaliphatic, olefinic, cycloolefinic system which may contain heteroatoms, preferably nitrogen, oxygen or sulfur, a metallocene, in particular 1,1'- or 1,2-disubstituted ferrocene, or particularly preferably an aromatic or heteroaromatic ring system which may be unsubstituted or be substituted by one or more substituents as indicated for $R^1$–$R^5$ or directly substituted by $C_1$–$C_{10}$-alkoxy, $C_1$–$C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-(alkyl-$C_1$–$C_8$)$_2$, N-(aryl-$C_5$–$C_6$)$_2$, N-(alkyl-$C_1$–$C_8$)$_3{}^+$, N-(aryl-$C_5$–$C_6$)$_3{}^+$, cyano, carboxylato of the formulae COOH and COOR$^8$, where R$^8$ is either a monovalent cation or $C_1$–$C_8$-alkyl, $C_1C_6$-acyloxy, sulfinato, sulfonato of the formulae SO$_3$H and SO$_3$R$^8$, where R$^8$ is either a monovalent cation, $C_1$–$C_8$-alkyl or $C_6$-aryl, phosphonato, phosphato of the formulae PO$_3$H$_2$, PO$_3$HR$^8$ and PO$_3$R$^8_2$, where R$^8$ is either a monovalent cation, $C_1$–$C_8$-alkyl or $C_6$-aryl, $C_1$–$C_6$-trialkylsilyl, CONH$_2$, NHCO-alkyl-$C_1$–$C_4$, CON(alkyl-$C_1$–$C_8$)$_2$, CO-alkyl-$C_1$–$C_8$, COO-alkyl-$C_1$–$C_8$, CO-alkenyl-$C_1$–$C_8$, NHCOO-alkyl-$C_1$–$C_4$, CO-aryl-$C_6$–$C_{10}$, COO-aryl-$C_6$–$C_{10}$, CHCH—COO-alkyl-$C_1$–$C_8$, CHCHCOOH and P is trivalent phosphorus.

The invention also relates to complexes comprising such a chiral ligand system of the formula (I) with at least one metal.

R$^1$–R$^5$ are each preferably, independently of one another, a $C_1$–$C_{20}$-alkyl, alkenyl, haloalkyl, cycloalkyl, cycloalkenyl, aryl, heteroaryl radical, each of which may be substituted by one or more substituents selected from the group consisting of $C_1$–$C_{20}$-alkyl, $C_2$–$C_{20}$-alkenyl, $C_1$–$C_{10}$-haloalkyl, $C_3$–$C_8$-cycloalkyl, $C_3$–$C_8$-cycloalkenyl, $C_6$–$C_{14}$-aryl, $C_2$–$C_7$-heteroaryl, $C_1$–$C_{10}$-alkoxy, halo, nitro, hydroxy, oxo, thio, thiolato, amino, substituted amino, cyano, sulfonato, tri-$C_1$–$C_6$-alkylsilyl, where two of the substituents may also be bridged.

Preference is given to compounds in which Z is part of a ring system. R$^3$ is not part of this ring system. Preference is given to three- to nine-membered ring systems. Particular preference is given to five- to seven-membered ring systems. The ring system can contain from one to four heteroatoms, preferably from one to two heteroatoms, which are preferably selected from among O, N and S. Sulfur S can be present in various oxidation states, preferably —S— or —SO$_2$—. The nitrogen of the ring system can be present as NR, NR$_2^+$, NRH$^+$, NC(O)R, NSO$_2$R, NO(O)R$_2$, where R is alkyl or aryl. The ring systems can be directly substituted by one or more substituents as indicated for R$^1$–R$^5$ or by alkoxy, halo, nitro, hydroxy, oxo, thio, thiolato, amino, substituted amino, cyano, sulfonato, phosphonato, trialkylsilyl groups, where the substituents can also be bridged to one another.

Preferred ring systems are phenyl, cyclopentyl, cyclohexyl, pyridyl, pyrrole, furyl, thiophene, tetrahydrofuran, tetrahydrothiophene, piperidyl, pyrrolidinyl, ferrocenyl, dioxolane or sulfolane rings which may be unsubstituted or substituted as described above. For the purposes of the present invention, metallocenes such as ferrocenes are formally included among aromatics.

In the ligand system of the present invention, R$^1$–R$^7$ preferably comprise, independently of one another, alkyl, alkenyl, cycloalkyl, cycloalkenyl, alkoxy, trialkylsilyl or/and dialkylamino groups having from 1 to 20, in particular from 1 to 6, carbon atoms.

Among alkyl substituents, preference is given to methyl, ethyl, n-propyl, 1-methylethyl, n-butyl, 1-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl.

Among cyclic alkyl substituents, particular preference is given to substituted and unsubstituted cyclopentyl, cyclohexyl, cycloheptyl.

Preferred alkenyl radicals are vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl; 2-heptenyl, 1-octenyl or 2-octenyl. Among cyclic alkenyl substituents, particular preference is given to cyclopentenyl, cyclohexenyl, cycloheptenyl and norbornyl.

Among aryl substituents in R$^1$–R$^7$, particular preference is given to 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, where the abovementioned alkyl and alkoxy groups preferably each contain from 1 to 6 carbon atoms, 3,5-trifluoromethyl, 4-trifluoromethyl, 2-sulfonyl, 3-sulfonyl, 4-sulfonyl or monohalogenated to tetrahalogenated phenyl and naphthyl. Preferred halogen substituents are F, Cl and Br.

All haloalkyl or/and haloaryl groups preferably have the formulae CHal$_3$, CH$_2$CHal$_3$, C$_2$Hal, where Hal can be, in particular, F, Cl and Br. Particular preference is given to haloalkyl or/and haloaryl groups of the formulae CF$_3$, CH$_2$CF$_3$, C$_2$F$_5$.

Preference is given to systems in which when X is NR$^6_1$ Y is a direct phosphorus-carbon bond, and when X is O, Y is either a direct phosphorus-carbon bond or —O—. Finally, ligand systems of the formula I enriched in one enantiomer are preferred as optically active ligand systems. Particular preference is given to ligand systems whose enantiomeric enrichment exceeds 90%, in particular 99%.

A number of routes are available for synthesizing these compounds of the formula (I):

The choice of a reaction route is dependent on the availability of the corresponding starting materials and on the desired substitution pattern. In the following, an illustrative selection will be presented by way of example to indicate the variety of ligand systems obtainable by means of the novel process described here, without ruling out alternative synthetic routes and other substitution patents and ligand frameworks of the type (I). In the following description, the substituents R and R' represent different substituents specified more precisely in the above definition of R$^1$–R$^5$. In the interests of clarity, simple ligand frameworks such as phenyl or ethylene have been chosen in the illustrations, without thereby implying restrictions or limitations.

The synthetic principle for six basic structures of the type (I) is described below.

Variation of methods which are known in principle makes it possible to obtain phosphine alcohols and phosphineamines of the type III, V, VII, VIII, X and XI (schemes 2–4) in a few synthesis steps. These routes will be described briefly for the purposes of illustration.

Chiral alcohols of the type II (scheme 1) (obtainable by various asymmetric reduction methods. Hydrogenation: e.g. Noyori et al., Tetrahedron Letters, 1991, 32, 4163; J. Am. Chem. Soc. 1998, 120, 13529; hydride reduction: e.g. Corey et al., J. Am. Chem. Soc. 1987, 109, 5551) can, after introduction of a suitable alcohol-protecting group SG (e.g. methoxymethylene, Fuji et al., Synthesis, 1975, 276; tetrahydropyranyl, Weiss et al., J. Org. Chem. 1979, 44, 1438), be metallated and subsequently quenched with the desired chlorophosphine (Brunner et al., J. Chem. Soc., Perkin Trans. 1, 1996). After splitting off the protecting group SG under acid conditions, the desired chiral phosphinoalcohol, illustrated by structure III in FIG. 1, is obtained.

Scheme 1

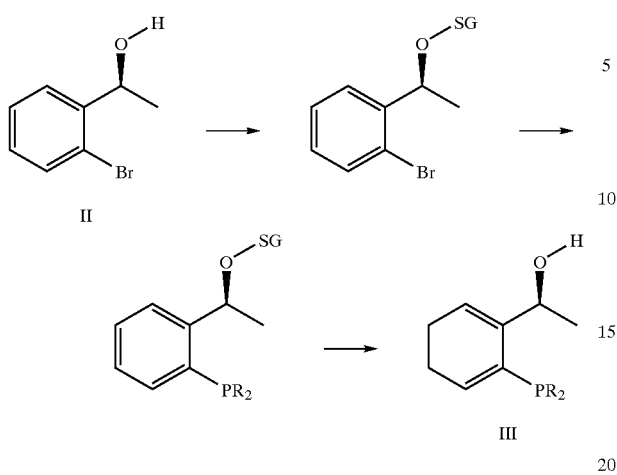

The corresponding chiral aminophosphines of the type V (scheme 2) are obtainable via a similar reaction sequence. Starting from chiral amines of the type IV (obtainable according to processes known in principle by means of various asymmetric reduction methods (hydrogenation: Burk et al., J. Org. Chem. 1998, 63, 6084; J. Am. Chem. Soc. 1996, 118, 5142; hydride transfer: Mukaiyama et al., Chem. Lett. 1997, 493; enzymatically: Santaniello et al., Chem. Rev. 1992, 92, 1071)), after N-alkylation and protection of the NH function, the compounds are phosphinated as above and the secondary aminophosphine V is subsequently set free.

Scheme 2

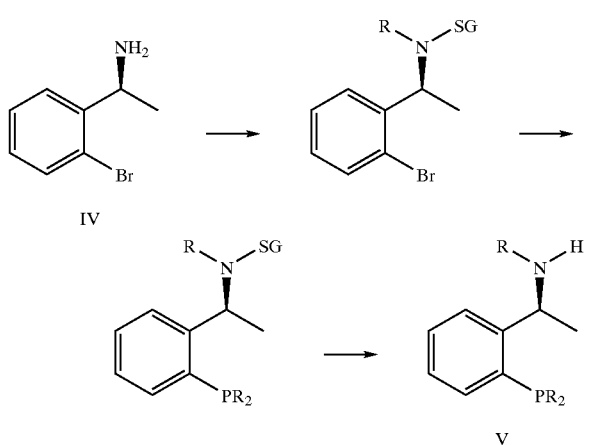

Aminophosphines and hydroxyphosphines having a ferrocenyl bridge (VII and VIII) (scheme 3) are likewise obtainable by modification of known synthesis strategies. Starting from enatiomerically pure aminoferrocenylphosphine (VI) (synthesis, for example: Hayashi and Kumada, Bull. Chem. Soc. Jpn., 1980, 53, 53, 1138), the corresponding sec-hydroxyferrocenylphosphines (VII) or aminoferrocenylphosphines (VIII) can be obtained with retention of the configuration by means of various nucleophilic substitution reactions (methods analogous to Ugi et al., J. Org. Chem. 37, 3052, and Hayashi and Kumada, Bull. Chem. Soc. Jpn., 1980, 53, 1138).

Scheme 3

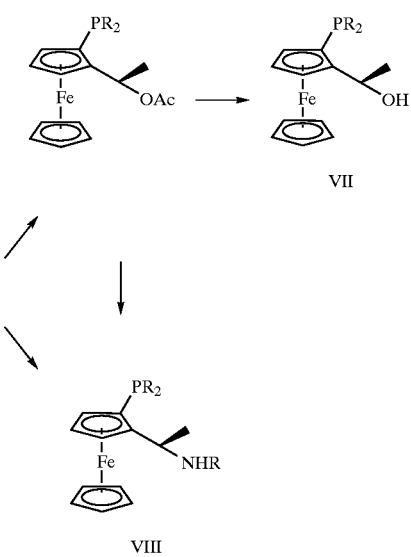

Borane-protected hydroxyphosphines having an alkyl bridge (X) (scheme 4) can be prepared by enantioselective diorganozinc addition onto phosphinylaldehydes (IX) using a method analogous to Brunner et al. (Tetrahedron Lett. 1998, 54, 10317). Corresponding aminophosphines (XI) can be obtained from the phosphinylaldehydes (IX) by reductive amination with primary amines and subsequent resolution of the racemate.

Scheme 4

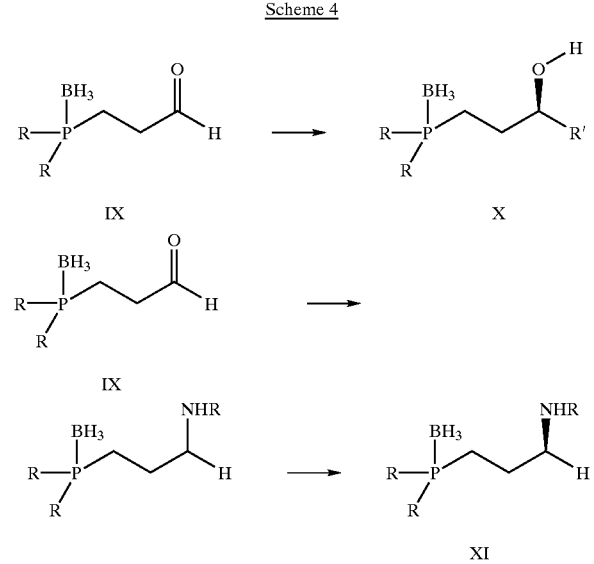

According to the invention, the conversion of the aminophosphines and hydroxyphosphines III, V, VII, VIII into the novel ligand systems XII–XVII of the formula (I) (scheme 5) occurs in one step by addition of chlorophosphines or chlorophosphites in the presence of stoichiometric amounts of a base (methods for substitution reactions of this type: e.g. Reetz et al., Angew. Chem. 1999, 111, 134; RajanBabu et al., J. Org. Chem. 1997, 62, 6012; Onuma et al., Bull. Chem. Soc. Jpn. 1980, 53, 2012). For the compounds of the type X and XI, subsequent removal of the protective borane group, e.g. by means of amines, is necessary.

Scheme 5

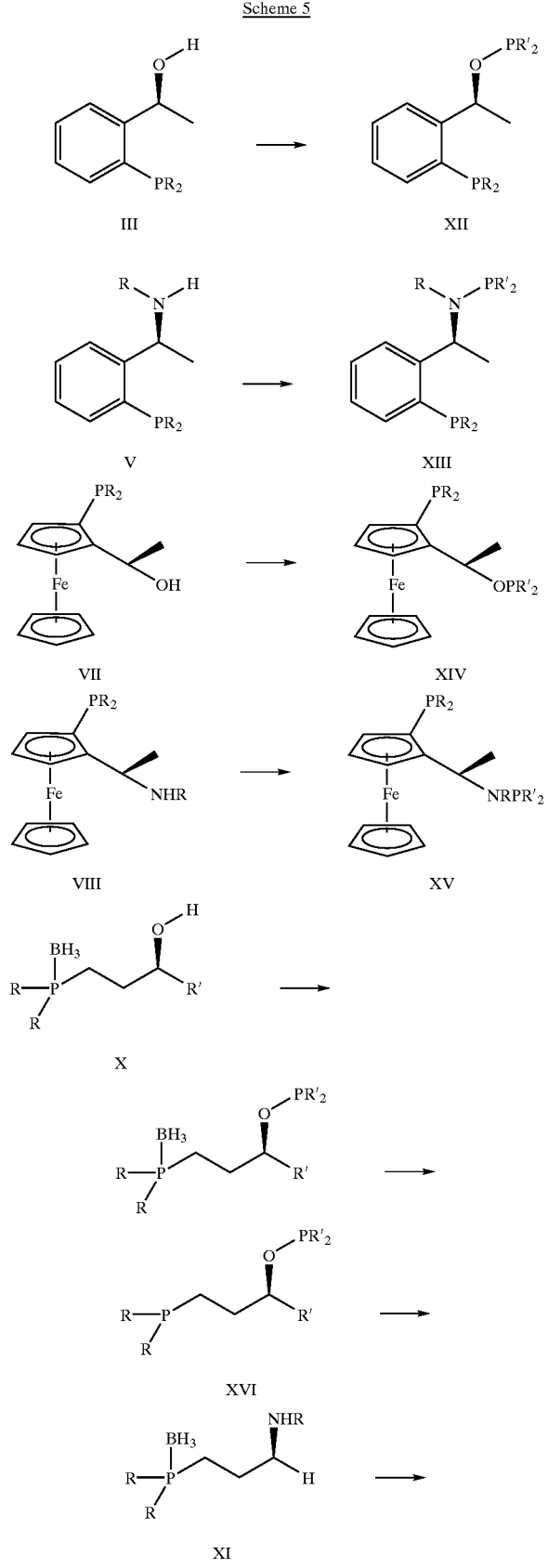

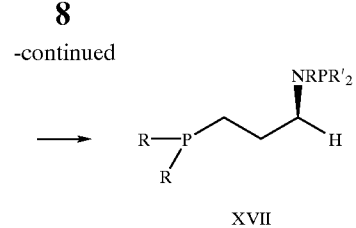

According to the invention, ligands of the type 1 in which the substituents $R^1$, $R^2$, $R^4$ and $R^5$ are identical can, as an alternative, be prepared in a single-vessel process starting from the corresponding haloalcohols of the type II by reaction with 2 equivalents of a strong base (e.g. tert-butyllithium) and subsequent reaction with 2 equivalents of the corresponding chlorophosphines (scheme 6).

Scheme 6

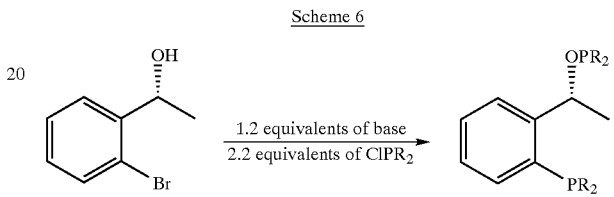

The compounds of the formula (I) can be used as ligands on metals in asymmetric, metal-catalyzed reactions (e.g. hydrogenation, hydroformylation, rearrangement, allylic alkylation, cyclopropanation, hydrosilylation, hydride transfers, hydroboration, hydrocyanation, hydrocarboxylation, aldol reactions or the Heck reaction) and also in polymerizations. They are particularly suitable for asymmetric reactions.

Suitable complexes, in particular of the formula (XVIII), comprise novel compounds of the formula (I) as ligands, $$[M_xP_mL_nS_q]A_r \qquad (XVIII)$$

where, in the formula (XVIII), M is a metal center, preferably a transition metal center, L are identical or different coordinating organic or inorganic ligands and P are novel bidentate organophosphorus ligands of the formula (I), S are coordinating solvent molecules and A are equivalents of noncoordinating anions, and x and m are integers greater than or equal to 1, n, q and r are integers greater than or equal to 0.

An upper limit is imposed on the sum m+n+q by the coordination sites available on the metal centers, with not all coordination sites having to be occupied. Preference is given to complexes having an octahedral, pseudooctahedral, tetrahedral, pseudotetrahedral, square planar coordination sphere, which may also be distorted, around the respective transition metal center. In such complexes, the sum m+n+q is less than or equal to 6x.

The complexes of the invention contain at least one metal atom or ion, preferably a transition metal atom or ion, in particular one selected from the group consisting of palladium, platinum, rhodium, ruthenium, osmium, iridium, cobalt, nickel and copper.

Preference is given to complexes having less than four metal centers, particular preferably ones having one or two metal centers. The metal centers can be occupied by different metal atoms and/or ions.

Preferred ligands L in such complexes are halide, in particular Cl, Br and I, diene, in particular cyclooctadiene, norbornadiene, olefin, in particular ethylene and cyclooctene, acetato, trifluoroacetato, acetylacetonato, allyl, methallyl, alkyl, in particular methyl and ethyl, nitrile, in particular acetonitrile and benzonitrile, and also carbonyl and hydrido ligands.

Preferred coordinating solvents S are amines, in particular triethylamine, alcohols, in particular methanol, and aromatics, in particular benzene and cumene.

Preferred noncoordinating anions A are trifluoroacetate, trifluoromethanesulfonate, $BF_4$, $ClO_4$, $PF_6$, $SbF_6$ and $BAr_4$.

In the individual complexes, different molecules, atoms or ions can be present in the individual constituents M, P, L, S and A.

Among the complexes having an ionic structure, preference is given to compounds of the type $[RhP(diene)]^+A^-$, where P is a novel ligand of the formula (I).

These metal-ligand complexes can be prepared in situ by reaction of a metal salt or an appropriate precursor complex with the ligands of the formula (I). Furthermore, a metal-ligand complex can be obtained by reaction of a metal salt or an appropriate precursor complex with the ligands of the formula (I) and subsequent isolation.

Examples of metal salts are metal chlorides, bromides, iodides, cyanides, nitrates, acetates, acetylacetonates, hexafluoroacetylacetonates, tetrafluoroborates, perfluoroacetates and triflates, in particular of palladium, platinum, rhodium, ruthenium, osmium, iridium, cobalt, nickel or/and copper.

Examples of precursor complexes are: cyclooctadienepalladium chloride, cyclooctadienepalladium iodide, 1,5-hexadienepalladium chloride, 1,5-hexadienepalladium iodide, bis(dibenzylidene-acetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide, bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, tetramethylethylenediaminedimethylpalladium, cyclooctadieneplatinum chloride, cyclooctadieneplatinum iodide, 1,5-hexadieneplatinum chloride, 1,5-hexadieneplatinum iodide, bis(cyclooctadiene)platinum, potassium ethylenetrichloroplatinate, cyclooctadienerhodium(I) chloride dimer, norbornadienerhodium(I) chloride dimer, 1,5-hexadienerhodium(I) chloride dimer, tris(triphenylphosphine)rhodium(I) chloride, hydridocarbonyltris(triphenylphosphine)rhodium(I) chloride, bis(cyclooctadiene)rhodium(I) perchlorate, bis(cyclooctadiene)rhodium(I) tetrafluoroborate, bis(cyclooctadiene)rhodium(I) triflate, bis(acetonitrile)cyclooctadienerhodium(I) perchlorate, bis(acetonitrile)cyclooctadienerhodium(I) tetrafluoroborate, bis(acetonitrile)cyclooctadienerhodium(I) triflate, cyclopentadienerhodium(III) chloride dimer, pentamethylcyclopentadienerhodium(III) chloride dimer, (cyclooctadiene)Ru($\eta^3$-allyl)$_2$, ((cyclooctadiene)Ru)$_2$(acetate)$_4$, ((cyclooctadiene)Ru)$_2$(trifluoroacetate)$_4$, $RuCl_2$(arene) dimer, tris(triphenylphosphine)ruthenium(II) chloride, cyclooctadieneruthenium(II) chloride, $OsCl_2$(arene) dimer, cyclooctadieneiridium(I) chloride dimer, bis(cyclooctene)iridium(I) chloride dimer, bis(cyclo-octadiene)nickel, (cyclododecatriene)nickel, tris(norbornene)nickel, nickel tetracarbonyl, nickel (II) acetylacetonate, (arene)copper triflate, (arene)copper perchlorate, (arene)copper trifluoroacetate, cobalt carbonyl.

The complexes based on one or more metals, in particular those selected from the group consisting of Ru, Co, Rh, Ir, Ni, Pd, Pt, Cu, may themselves be catalysts or can be used for preparing catalysts based on one or more metals, in particular those selected from the group consisting of Ru, Co, Rh, Ir, Ni, Pd, Pt, Cu. All these complexes are suitable for hydrogenation, hydroformylation, rearrangement, allylic alkylation, cyclopropanation, hydrosilylation, hydride transfer reactions, hydroboration, hydrocyanation, hydrocarboxylation, aldol reactions or the Heck reaction. The complexes of the invention are particularly useful in the asymmetric hydrogenation of C=C, C=O or C=N bonds, in which they have high activities and selectivities, and in asymmetric hydroformylation. In particular, it is here advantageous that the ligands of the formula (I) can be very well matched to the respective substrate and the catalytic reaction in terms of their steric and electronic properties due to the simple and wide-ranging manner in which they can be modified.

Corresponding catalysts comprise at least one of the complexes of the invention.

EXAMPLES

General

Reactions of air-sensitive compounds were carried out in an argon-filled glove box or in standard Schlenk tubes. Tetrahydrofuran (THF), diethyl ether and dichloromethane solvents were degassed and dried by means of a solvent drying unit (Innovative Technologies) by filtration through a column filled with activated aluminum oxide; toluene and pentane were additionally freed of oxygen by means of a column filled with a copper catalyst.

The following examples serve to illustrate the invention, but they do not imply any restriction.

Synthesis of Chiral Alcohols

The following synthetic methods describe, by way of example, possible ways of carrying out the chiral reduction of aromatic ketones.

Example 1

Preparation of (R)-2-bromophenylethan-1-ol (Scheme 7)

Using the general methods of Noyori et al., a solution of bromoacetophenone (78.5 mmol) and [Ru(R-BINAP)Cl$_2$] (0.079 mmol) in 30 ml of methanol is stirred at 70° C. under 35 bar of H$_2$ for 3 hours. The solvent is removed under reduced pressure and the crude product is distilled at 130–140° C. and 2–3 bar in a bulb tube. The colorless oil is crystallized from pentane at −20° C.

Yield: 76%; ee>99%.

$^1$H-NMR (CDCl$_3$): δ=7.58 (dd, 1H, Ar), 7.52 (dd, 1H, Ar), 7.35 (dd, 1H, Ar), 7.05 (m, 1H, Ar), 5.25 (q, 1H, J=6.0 Hz, CHOH), 1.96 (s, br, 1H, OH), 1.49 (d, 3H, J=6.0 Hz, CH$_3$) ppm.

Scheme 7

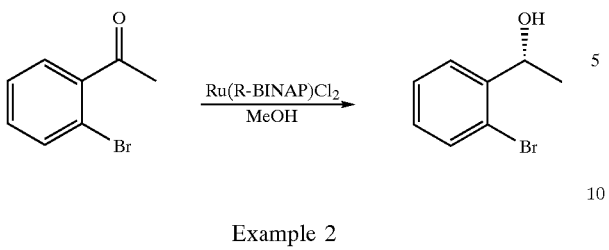

Example 2

Preparation of (R)-2,5-dimethyl-4-bromo-3-(1-hydroxyethyl)thiophene (Scheme 8)

3-Acetyl-4-bromo-2,5-dimethylthiophene (78.5 mmol) was reduced by means of Ipc$_2$BCl in tetrahydrofuran using the general method of Brown et al. (J. Org. Chem. 1989, 54, 4504).

Yield: 71% (ee=72%).

$^1$H-NMR (CDCl$_3$): δ=5.07 (dq, C$\underline{H}$OH), 2.47 (s, CH$_3$), 2.30 (s, CH$_3$), 1.52 (d, CH$_3$) ppm.

Scheme 8

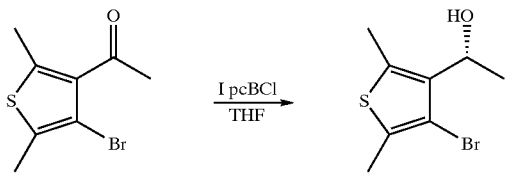

Example 3

General Method for the Synthesis of Racemic Alcohols

The corresponding ketone is dissolved in methanol and added dropwise to a methanolic suspension of 2 equivalents of sodium borohydride and the mixture is stirred at room temperature for 24 hours. The reaction mixture is poured into cold saturated ammonium chloride solution and the methanol is removed under reduced pressure. The aqueous phase is extracted three times with ethyl acetate, the combined organic phases are dried over magnesium sulfate and the solvent is subsequently removed under reduced pressure. The crude racemic product is purified by vacuum distillation or low temperature crystallization.

Synthesis of the Ligands of the Invention
General Method for the Synthesis of the Ligands of the Invention by a Single-vessel Process A solution of the corresponding alcohol (10.6 mmol) (for examples, see Scheme 9) in 40 ml of tetrahydrofuran (THF) is cooled to −78° C. and t-butyllithium (25.0 mmol) is added over a period of 15 minutes. The reaction solution is stirred for another one hour at −70° C. and sub sequently admixed with chlorodiphenylphosphine (22 mmol in 7 ml of THF). The reaction solution is warmed to room temperature overnight and stirred for 15 hours. The solution is evaporated to 10 ml under reduced pressure and subsequently admixed with 10 ml of pentane. It is filtered through Celite and the solvent is removed under reduced pressure. The residue is taken up in ether/pentane (3:2) and filtered through aluminum oxide (ALOX) (neutral) (eluant:ether/pentane 3:2). Removal of the solvent leaves a colorless or light-yellow oil which partly crystallizes after some time.

Scheme 9

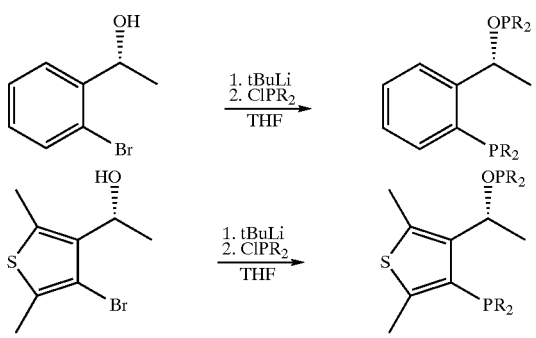

Example 4

Preparation of (R)-2-diphenylphosphino-1-(O-diphenylphosphinylethan-1-ol)benzene Yield: 76%

$^1$H-NMR (C$_6$D$_6$): δ=7.95–6.80 (m, 22H, Ar), 6.55 (m, 1H, Ar), 6.21 (m, 1H, Ar), 5.54 (m, 1H, C$\underline{H}$OP), 1.58 (d, 3H, J=5.8 Hz, CH$_3$) ppm.

$^{31}$P-NMR (C$_6$D$_6$): δ=109.9 (s, P—O) , −17.1 (s, P—C) ppm.

Example 5

Preparation of (R)-2-dicyclohexylphosphino-1-(O-dicyclohexylphosphinylethan-1-ol)-benzene Yield: 66%

$^1$H-NMR (C$_6$D$_6$): δ=7.58 (dd, 1H, Ar), 7.52 (dd, 1H, Ar), 7.35 (dd, 1H, Ar), 7.05 (m, 1H, Ar), 6.27 (m, 1H, C$\underline{H}$OP), 2.34–1.17 (m, 47H, Cy—H, CH$_3$) ppm.

$^{31}$P-NMR (C$_6$D$_6$): δ=144.8 (s, P—O), −17.6 (s, P—C) ppm.

Example 6

Preparation of (R)-2,5-dimethyl-4-diphenylphosphino-3-(O-diphenylphosphinylethan-1-ol)thiophene Yield: 81%

$^1$H-NMR (C$_6$D$_6$): δ=7.69–6.97 (m, 20H, Ar), 5.81 (m, 1H, C$\underline{H}$OP), 2.36 (s, 3H, CH$_3$), 2.03(s, 3H, CH$_3$), 1.55 (d, 3H, J=6.1 Hz, CH$_3$) ppm.

$^{31}$P-NMR (C$_6$D$_6$): δ=109.8 (s, P—O ), −25.7 (s, P—C) ppm.

Synthesis of the Ligands in a Multistage Process

Example 7

Preparation of (R)-2-bromo-1-(1-ethyl methoxymethyl ether)benzene (MOM ether) (Scheme 10)

Sodium hydride (28.9 mmol) was washed with pentane. After removal of the pentane, a suspension in 60 ml of THF was prepared and (R)-2-bromophenylethan-1-ol (19.2 mmol) was added a little at a time while cooling in ice. After addition was complete, the reaction mixture was stirred for 60 minutes, after which chloromethyl methyl ether was added over a period of 10 minutes while cooling in ice and the mixture was stirred overnight. The reaction solution is carefully hydrolyzed with saturated NH$_4$Cl solution. The aqueous phase is extracted three times with 100 ml of ethyl acetate, dried over sodium sulfate and the solvent is removed under reduced pressure. The crude product is distilled at 1.6 mbar and 120° C. in a bulb tube.

Yield: 86%

$^1$H-NMR (CDCl$_3$): δ=7.52 (m, 2H, Ar), 7.31 (m, 1H, Ar), 7.11 (m, 1H, Ar), 5.25 (q, 1H, J=6.0 Hz, CHOC), 4.61 (d, 1H, J=6.9 Hz, CH$_2$) 4.54 (d, 1H, J=6.9 Hz, CH$_2$), 3.39 (s, 3H, OCH$_3$), 1.45 (d, 3H, J=6.0 Hz, CH$_3$) ppm.

Scheme 10

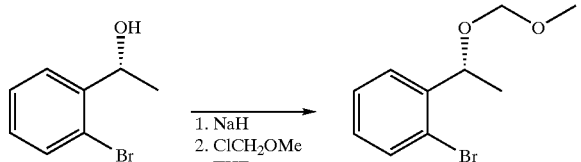

Example 8

Preparation of (R)-2-diphenylphosphino-1-(1-ethyl methoxymethyl ether)benzene (Scheme 11)

A solution of (R)-2-bromo-1-(ethyl 1-methoxymethyl ether)benzene (5.0 mmol) in 20 ml of THF was cooled to −78° C. and 2 equivalents of t-butyllithium were added over a period of 15 minutes. The reaction solution was stirred for another 90 minutes at −78° C. and subsequently admixed with 1.1 equivalents of chlorodiphenylphosphine (in 5 ml of THF) at −78° C. After 40 minutes, the reaction solution was warmed to room temperature and stirred for 15 hours. The reaction solution was hydrolyzed with saturated degassed NH$_4$Cl solution and the aqueous phase was extracted three times with 30 ml each time of toluene. The organic phases were dried over sodium sulfate and the solvent was removed under reduced pressure. The residue is taken up in ether/pentane (3:2) and filtered through ALOX (neutral) (eluant:ether/pentane 3:2). Removal of the solvent leaves a colorless oil. Yield: 1.64 g.

$^1$H-NMR (C$_6$D$_6$): δ=7.62–6.80 (m, 12H, Ar), 7.31 (m, 1H, Ar), 7.11 (m, 1H, Ar), 5.50 (m, 1H, CHOC), 4.40 (d, 1H, J=6.2 Hz, CH$_2$) 4.34 (d, 1H, J=6.2 Hz, CH$_2$), 3.19 (s, 3H, OCH$_3$), 1.25 (d, 3H, J=6.0 Hz, CH$_3$) ppm.

$^{31}$P-NMR (C$_6$D$_6$): δ=17.08 ppm.

Scheme 11

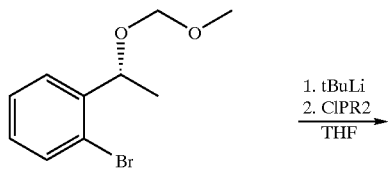

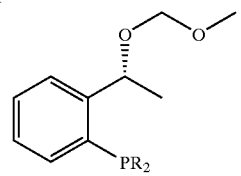

Example 9

Preparation of (R)-2-diphenylphosphino-phenyl (ethan-1-ol) (Scheme 12)

(R)-2-Diphenylphosphino-1-(1-ethyl methoxymethyl ether) benzene was dissolved in 40 ml of dichloromethane and 10 ml of methanol, admixed with p-toluenesulfonic acid and stirred at 40° C. for 4 hours. 30 ml of sodium hydrogen carbonate solution were added to this reaction solution and the aqueous phase was extracted twice with dichloromethane. The organic phase was dried over magnesium sulfate and the solvent was removed under reduced pressure. The product is isolated as an oil.

Yield: 53%.

$^1$H-NMR (C$_6$D$_6$): δ=7.60–7.05 (m, 13H, Ar), 6.75 (m, 1H, Ar), 5.55 (m, 1H, CHOH), 2.85 (br, 1H, OH) 1.27 (d, 3H, CH$_3$) ppm.

$^{31}$P-NMR (C$_6$D$_6$): δ=17.4 ppm.

Scheme 12

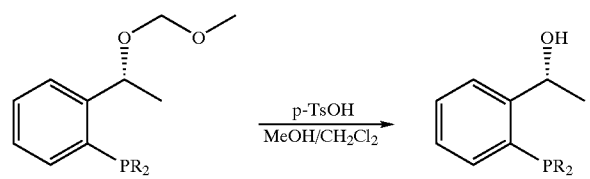

Example 10

Preparation of (R)-2-bromo-1-(1-ethyl tetrahydropyranyl ether)benzene ((R)-THP ether) (Scheme 13)

0.92 mmol of p-toluenesulfonic acid are added to an ice cold solution of 20 mmol of (R)-2-bromophenyl-1-(ethan-1-ol) in 20 ml of dichloromethane. 22.1 mmol of 3,4-dihydropyran are added over a period of 2 minutes, the solution is warmed to room temperature and stirred for another 1.5 hours. The reaction solution is hydrolyzed with 20 ml of sodium hydrogen carbonate solution, the aqueous phase is extracted twice with dichloromethane and the organic phase is washed with water. After drying over magnesium sulfate, the solvent is removed under reduced pressure. The crude product is purified by means of column chromatography (dichloromethane/hexane 1:1→3:1). Yield: 64% (diastereomer ratio 4:1)

$^1$H-NMR (CDCl$_3$): δ=7.67–7.35 (m, 3H, Ar), 7.12 (m, 1H, Ar), 5.15 (m, 0.8H, CHO-THP), 5.00 (m, 0.2H, CHO-THP*), 4.75 (m, 0.2H, OCHO), 4.25–4.75 (m, 0.8H, OCHO), 3.84 (m, 0.8H, CHHO), 3.52 (m, 0.2H, CHHO), 3.39 (m, 0.8H, CHHO), 3.23 (m, 0.2H, CHHO), 1.80–1.35 (m, 6H, THP), 1.32 (d, 2.4H, J=6.4 Hz, CH$_3$), 1.29 (d, 0.6H, J=6.4 Hz CH$_3$) ppm.

Scheme 13

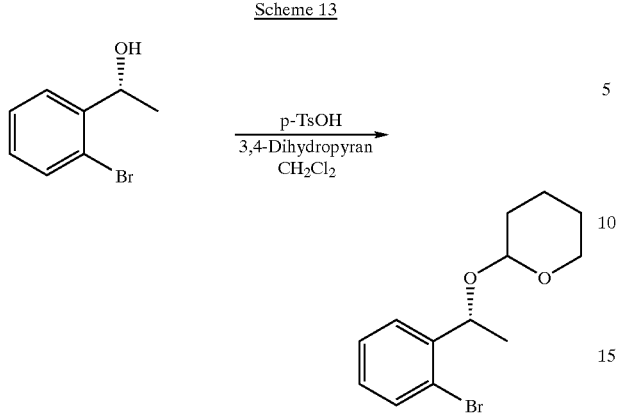

Example 11

Preparation of (R)-2-diphenylphosphino-1-(1-ethyl tetrahydropyranyl ether)benzene-borane-adduct (Scheme 14)

t-Butyllithium (23.5 mmol) is added over a period of 10 minutes to a solution of (R)-THP ether (11.7 mmol in 34 ml of THF) which has been cooled to −78° C. and the yellow solution is stirred at −78° C. for one hour. Chlorodiphenylphosphine (11.7 mmol) is added to this solution and the solution is warmed to room temperature for 30 minutes. The reaction solution is again cooled to −78° C., admixed with 35.2 mmol of borane-THF complex and warmed to room temperature overnight. The reaction mixture is hydrolyzed with ice water and admixed with 90 ml of tert-butyl methyl ether and 65 ml of 1M hydrochloric acid. Phase separation is obtained after addition of 50 ml of dichloromethane. The aqueous phase is extracted twice with dichloromethane, washed with saturated sodium chloride solution and dried over magnesium sulfate. Removal of the solvent gives the crude product as a white solid and this is reacted further without purification.

Yield: 6.24 g $^{31}$P-NMR (CDCl$_3$): δ=20.5 (s, BH$_3$→P—C) ppm.

Scheme 14

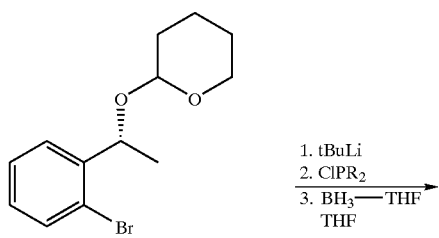

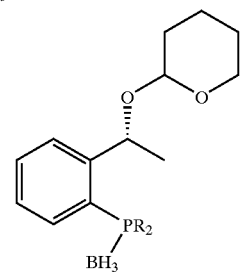

Example 12

Preparation of (R)-2-diphenylphosphino-1-(ethan-1-ol)benzene Borane Adduct (Scheme 15)

The borane complex (12 mmol) is dissolved in 20 ml of methanol and 5 ml of dichloromethane. 0.6 mmol of toluenesulfonic acid are added to this solution and the mixture is stirred for 6 hours while warming gently, after which the solvent is removed under reduced pressure. The crude product is purified by means of flash chromatography (ethyl acetate/hexane 2:8→3:7). The product from which the borane group has been split off was isolated as second fraction.

$^1$H-NMR (CDCl$_3$): δ=7.73 (m, 1H, Ar), 7.62–7.40 (m, 11H, Ar), 7.21 (m, 1H, Ar), 6.87 (m, 1H, Ar), 5.20 (q, 1H, J=6.4 Hz, C$\underline{H}$OH), 1.7 (s, br, 1H, OH), 1. 23 (d, 3H, J=6.4 Hz) ppm.

$^{31}$P-NMR (CDCl$_3$): δ=20.2 (s, BH$_3$→P—C) ppm.

Scheme 15

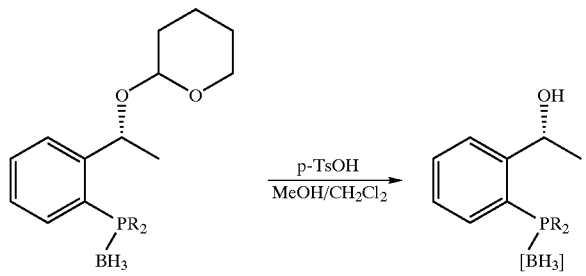

Example 13

Preparation of (R)-2-diphenylphosphino-1-(ethan-1-ol)benzene (Scheme 16)

The borane complex (15.9 mmol) is dissolved in 31 ml of methanol and 6 ml of dichloromethane. 0.79 mmol of toluenesulfonic acid are added to this solution and the mixture is stirred for 24 hours while warming gently, after which the solvent is removed under reduced pressure. The crude product is purified by means of flash chromatography (ethyl acetate/hexane 2:8→3:7).

Yield: 51%.

$^1$H-NMR (CDCl$_3$): δ=7.52–7.09 (m, 13H, Ar), 6.83 (m, 1H, Ar), 5.57 (m, 1H, C$\underline{H}$OH), 1.82 (m, br, 1H), 1.27 (d, 3H, J=6.4 Hz) ppm.

$^{31}$P-NMR (CDCl$_3$): δ=15.8 (s) ppm.

Scheme 16

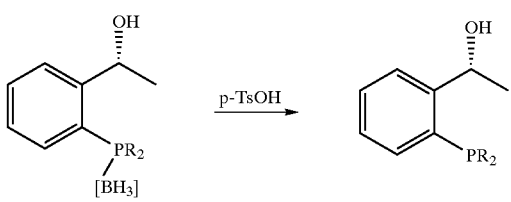

Example 15

Preparation of (R)-2-diphenylphosphino-1-(O-diisopropylphosphinoethan-1-ol)benzene (Scheme 17)

A solution of 2-diphenylphosphino-1-(ethan-1-ol)benzene (3.6 mmol) in 5 ml of THF is cooled to 0° C. and admixed with 4.2 mmol of triethylamine. 4.2 mmol of chlorodiisopropylphosphine are subsequently added over a period of 5 minutes by means of a syringe. The reaction solution is stirred at 0° C. for 2 hours and subsequently at room temperature for a further 2 hours. The solution is concentrated under reduced pressure and subsequently admixed with 3 ml of pentane and 5 ml of diethyl ether and filtered through ALOX (neutral) (eluant ether/pentane 3:2). Removal of the solvent gives the product as a light yellow oil.

$^{31}$P-NMR (CDCl$_3$): δ=134.0 (s, P—O), −16.1 (s, P—C) ppm.

Scheme 17

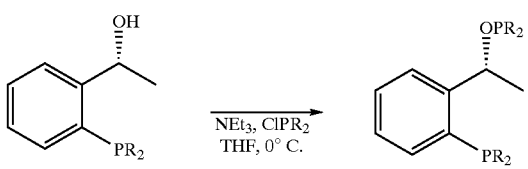

Example 15

Preparation of (R)-1-[(S)-2-diphenylphosphinoferrocenyl]-(o-diphenylphosphino-ethanol)

The preparation of (R)-1-[(S)-2-diphenylphosphino, ferrocenyl]ethanol was carried out as described by Hayashi et al., Bull. Chem. Soc. Jpn. 1980, 53, 1138. 60 mg (0.14 mmol) of (R)-1-[(S)-2-diphenylphosphino, ferrocenyl]ethanol are reacted with chlorodiphenylphosphine in THF using a method analogous to Example 14, but in the presence of pyridine as base. The crude product of the reaction indicates reaction to the desired.

$^{31}$P-NMR (CDCl$_3$): δ=98.4 (s, P—O), −21.2 (s, P—C) ppm.

Metal Complexes According to the Invention

General Preparation of the Metal Complexes 0.11 mmol of metal salt are dissolved in 4 ml of dichloromethane. 0.11 mmol of the ligand (dissolved in 1 ml of dichloromethane) are added to this solution and the solution is stirred for 30 minutes. The complex is precipitated from the clear orange solution by addition of pentane.

Example 16

K$^2$P,P'-{[(R)-2-Diphenylphosphino-1-(O-diphenylphosphinylethan-1-ol)benzene]cyclo-octadienylrhodium} triflate (Scheme 18)

Yield: 94%

$^{31}$P-NMR (CD$_2$Cl$_2$): δ=125.4 (dd, J$_{Rhp}$=165.1 Hz, JP$_{PP}$=35.2 Hz), 17.5 (dd, J$_{Rhp}$=145.8 Hz, J$_{PP}$=35.2 Hz) ppm.

Scheme 18

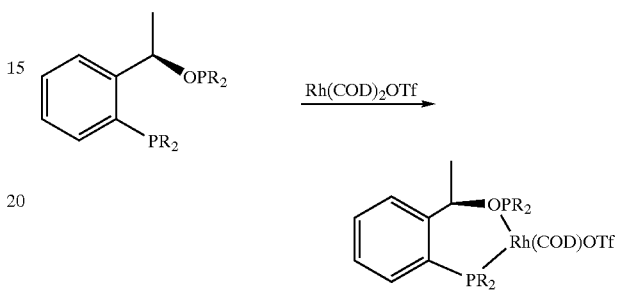

Example 17

K$^2$P,P'-{[((R)-2-Diphenylphosphinophenyl-O-diphenylphosphinylethan-1-ol)dichloro-palladium (Scheme 19)

Yield: 91%

$^{31}$P-NMR (CD$_2$Cl$_2$): δ=117.4 (s, P—O), 19.1 (s, P—C) ppm.

Scheme 19

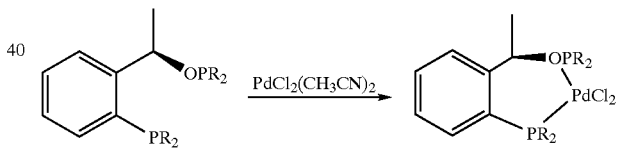

Example 18

K$^2$P,P'-{[(R)-2,5-Dimethyl-4-diphenylphosphino-3-(O-diphenylphosphinylethan-1-ol)-thiophene] cyclooctadienylrhodium} triflate (Scheme 20)

Yield: 93%

$^{31}$P-NMR (CD$_2$Cl$_2$): δ=120.5 (dd, J$_{RhP}$=160 Hz, J$_{PP}$31 Hz), 6.6 (dd, J$_{Rhp}$=141 Hz, J$_{PP}$=31 Hz) ppm.

Scheme 20

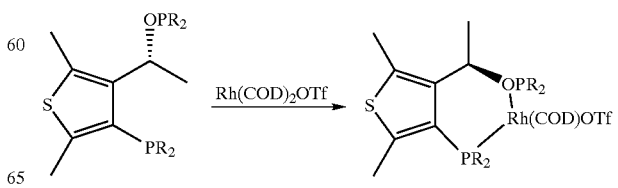

Example 19

K²P,P'-[(R)-2,5-Dimethyl-4-diphenylphosphino-3-(O-diphenylphosphinylethan-1-ol)-thiophene] dichloropalladium (Scheme 21)

Yield: 96%

³¹P-NMR (CD₂Cl₂): δ=116.8 (s) , 18.8 (s) ppm.

Scheme 21

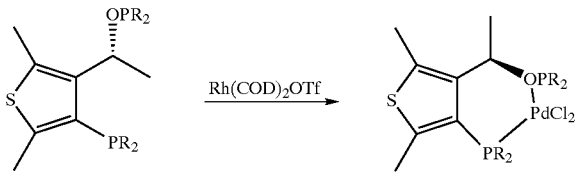

What is claimed is:

1. A bidendate organophosphorus ligand of the formula (I), $$R^1R^2PZC^*HR^3XP(YR^4)(YR^5) \quad (I)$$

where $R^1$–$R^5$ are identical or different and are a hydrogen atom or a $C_1$–$C_{50}$ group, X is —O—, —S— or —NR⁶—, $R^6$ corresponds to one of the radicals defined for $R^1$–$R^5$, Y is a direct phosphorus-carbon bond, —O— or —NR⁷—, where $R^7$ corresponds to one of the radicals defined for $R^1$–$R^5$, Z represents 1 to 6 carbon atoms which are joined by single or double bonds and link the phosphine unit $PR^1R^2$ to the carbon center C*, where Z is part of an aliphatic, cycloaliphatic, olefinic, cycloolefinic system which may contain heteroatoms, a metallocene which may be unsubstituted or be substituted by one or more substituents as indicated for $R^1$–$R^5$ or directly substituted by $C_1$–$C_{10}$-alkoxy, $C_1$–$C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-(alkyl-$C_1$–$C_8$)₂, N-(aryl-$C_5$–$C_6$)₂, N-(alkyl-$C_1$–$C_8$)₃⁺, N-(aryl $C_5$–$C_6$)₃⁺, cyano, carboxylato of the formulae COOH and COOR⁸, where $R^8$ is either a monovalent cation, $C_1$–$C_8$-alkyl, $C_1$–$C_6$-acyloxy, sulfinato, sulfonato of the formulae $SO_3H$ and $SO_3R^8$, where $R^8$ is either a monovalent cation, $C_1$–$C_8$-alkyl or $C_6$-aryl, phosphonato, phosphato of the formulae $PO_3H_2$, $PO_3HR^8$ and $PO_3R^8{}_2$, where $R^8$ is either a monovalent cation, $C_1$–$C_8$-alkyl or $C_6$aryl, $C_1$–$C_6$-trialkylsilyl, $CONH_2$, NHCO-alkyl-$C_1$–$C_4$, CON(alkyl-$C_1$–$C_8$)₂, CO-alkyl-$C_1$–$C_8$, COO-alkyl-$C_1$–$C_8$, CO-alkenyl-$C_1$–$C_8$, NHCOO-alkyl-$C_1$–$C_4$, CO-aryl-$C_6$–$C_{10}$, COO-aryl-$C_6$–$C_{10}$, CHCH—COO-alkyl-$C_1$–$C_8$, CHCH-COOH and P is trivalent phosphorus.

2. A compound as claimed in claim 1, wherein $R^1$–$R^5$ are each, independently of one another, an alkyl, alkenyl, haloalkyl, cycloalkyl, cycloalkenyl, aryl, heteroaryl group which contains up to 20 carbon atoms and may be substituted by one or more substituents selected from the group consisting of $C_1$–$C_{20}$-alkyl, $C_2$–$C_{20}$-alkenyl, $C_1$–$C_{10}$-haloalkyl, $C_3$–$C_8$-cycloalkyl, $C_3$–$C_8$-cycloalkenyl, $C_6$–$C_{14}$-aryl, $C_2$–$C_7$-heteroaryl, $C_1$–$C_{10}$-alkoxy, halo, nitro, hydroxy, oxo, thio, thiolato, amino, substituted amino, cyano, sulfonato, tri-$C_1$–$C_6$-alkylsilyl.

3. A compound as claimed in claim 1, wherein Z is part of a three- to nine-membered, preferably five- to seven-membered, ring system.

4. A compound as claimed in claim 3, wherein the ring system is an aromatic or heteroaromatic.

5. A compound as claimed in claim 4, wherein the aromatic is a 1,1'- or 1,2-substituted metallocene.

6. A compound as claimed in claim 5, wherein the metallocene is ferrocene.

7. A compound as claimed in claim 1, wherein the ring system Z contains from one to four heteroatoms.

8. A compound as claimed in claim 1, wherein the ring system Z contains one or two heteroatoms.

9. A compound as claimed in claim 3, wherein the ring systems are phenyl, cyclopentyl, cyclohexyl, pyridyl, pyrrole, furyl, thiophene, tetrahydrofuran, tetrahydrothiophene, piperidyl, pyrrolidinyl, dioxolane, ferrocenyl, sulfolane which may each be unsubstituted or substituted by one or more substituents as indicated for $R^1$–$R^5$ or directly substituted by $C_1$–$C_{10}$ alkoxy, $C_1$–$C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-(alkyl-$C_1$–$C_8$)₂, N-(aryl-$C_5$–$C_6$)₂, N-(alkyl-$C_1$–$C_8$)₃⁺, N-aryl-$C_5$–$C_6$)₃⁺, cyano, carboxylato of the formulae COOH and COOR⁸, where $R^8$ is either a monovalent cation or $C_1$–$C_8$-alkyl, $C_1$–$C_6$-acyloxy, sulfinato, sulfonato of the formulae $SO_3H$ and $SO_3R^8$, where $R^8$ is either a monovalent cation, $C_1$–$C_8$-alkyl or $C_6$-aryl, phosphonato, phosphato of the formulae $PO_3H_2$, $PO_3HR^8$ and $PO_3R^8{}_2$, where $R^8$ is either a monovalent cation, $C_1$–$C_8$-alkyl or $C_6$-aryl, $C_1$–$C_6$-trialkylsilyl, $CONH_2$, NHCO-alkyl-$C_1$–$C_4$, CON(alkyl-$C_1$–$C_8$)₂, CO-alkyl-$C_1$–$C_8$, COO-alkyl-$C_1$–$C_8$, CO-alkenyl-$C_1$–$C_8$, NHCOO-alkyl-$C_1$–$C_4$, CO-aryl-$C_6$–$C_{10}$, COO-aryl-$C_6$–$C_{10}$, CHCH—COO-alkyl-$C_1$–$C_8$, CHCHCOOH.

10. A compound as claimed in claim 1, wherein the heteroatoms are O, N or S.

11. A compound as claimed in claim 1, wherein $R^3$ is methyl or ethyl or isopropyl.

12. A compound as claimed in claim 1, wherein the alkyl, alkenyl, haloalkyl, cycloalkyl, cycloalkenyl, alkoxy, trialkylsilyl or/and dialkylamino groups in $R^1$–$R^7$ each contain, independently of one another, from 1 to 20, in particular from 1 to 6, carbon atoms.

13. A compound as claimed in claim 1, wherein the haloalkyl groups $R^1$–$R^7$ are $CF_3$, $CH_2CF_3$, $C_2F_5$.

14. A compound as claimed in claim 1, wherein $R^1$, $R^2$, $R^4$ and $R^5$ are aryl substituents.

15. A compound as claimed in claim 14, wherein the aryl substituents are 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, 3,5-trifluoromethyl, 4-trifluoromethyl, 2-sulfonyl, 3-sulfonyl, 4-sulfonyl, monohalogenated to tetrahalogenated phenyl, naphthyl.

16. A compound as claimed in claim 1, wherein $R^1$, $R^2$, $R^4$ and $R^5$ are alkyl substituents or cycloalkyl substituents.

17. A compound as claimed in claim 16, wherein the alkyl substituents are methyl, ethyl, n-propyl, 1-methylethyl, n-butyl, 1-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl.

18. A compound as claimed in claim 16, wherein the cyclic alkyl substituents are substituted and unsubstituted cyclopentyl, cyclohexyl, cycloheptyl.

19. A compound as claimed in claim 1, wherein X is $NR^6$ or O.

20. A compound as claimed in claim 1, wherein Y is $NR^7$, O or a direct phosphorus-carbon bond.

21. A compound of the formula I as claimed in claim 1, which is optically active.

22. A compound of the formula I as claimed in claim 1 which is enantiomerically enriched.

23. A compound as claimed in claim 22, wherein the enantiomeric enrichment exceeds 90%, preferably 99%.

24. A complex comprising a compound as claimed in claim 1 as ligand and at least one transition metal.

25. A complex as claimed in claim 24 which has the formula (XVIII),

   (XVIII)

where,

M is a metal center,

L are identical or different coordinating organic or inorganic ligands and

P are bidentate organophosphorus ligands of the formula (I),

S are coordinating solvent molecules and

A are equivalents of noncoordinating anions, where x and m are integers greater than or equal to 1, n, q and r are integers greater than or equal to 0.

26. A complex as claimed in claim 25, wherein the sum m+n+q is less than or equal to 6x.

27. A complex as claimed in claim 24 which has from 1 to 4 metal centers, preferably 1 or 2 metal centers.

28. A complex as claimed in claim 24 in which at least one metal center is a transition metal atom or ion, in particular palladium, platinum, rhodium, ruthenium, osmium, iridium, cobalt, nickel or/and copper.

29. A method for asymmetric reaction or polymerization comprising contacting the complex of claim 24 with one or more reactant(s).

30. A method for asymmetric reaction or polymerization comprising contacting the complex of claim 24 with one or more reactant(s), wherein the asymmetric reaction is hydrogenation, hydroformylation, rearrangement, allylic alkylation, cyclopropanation, hydrosilylation, hydride transfer reaction, hydroboration, hydrocyanation, hydrocarboxylation, aldol reaction or the Heck reaction.

31. A method for asymmetric hydrogenation and/or hydroformylation comprising contacting the complex of claim 24 with one or more reactant(s).

32. A bidendate organophosphorus ligand of claim 1, wherein $R^1$–$R^5$ are independently H, or $C_1$–$C_{24}$-alkyl, $C_2$–$C_{24}$-alkenyl, $C_3$–$C_8$-cycloalkyl, $C_3$–$C_8$-cycloalkenyl, $C_6$–$C_{14}$-aryl, phenyl, naphthyl, fluorenyl, $C_2$–$C_{13}$-heteroaryl, where the number of heteroatoms may be 1–4, and where the specified groups may each bear one or more substituents which may be selected independently from among hydrogen, $C_1$–$C_{20}$-alkyl, $C_2$–$C_{20}$-alkenyl, $C_1$–$C_{10}$-haloalkyl, $C_3$–$C_8$-cycloalkyl, $C_3$–$C_8$-cycloalkenyl, $C_2$–$C_9$-heteroalkyl, $C_1$–$C_9$-heteroalkenyl, $C_6$–$C_{14}$-aryl, phenyl, naphthyl, fluorenyl, $C_2$–$C_7$-heteroaryl, where the number of heteroatoms may be 1–4, $C_1$–$C_{10}$-alkoxy, $C_1$–$C_9$-trihalomethylalkyl, trifluoromethyl, tri-chloromethyl, fluoro, chloro, bromo, iodo, nitro, hydroxy, trifluoromethylsulfonato, oxo, thio, thiolato, amino, $C_1$–$C_8$-substituted amino of the forms mono-, di-, tri-$C_1$–$C_8$-alkylamino or $C_2$–$C_8$-alkenylamino or mono-, di-, tri-$C_6$–$C_8$-arylamino or $C_1$–$C_8$-alkyl-$C_6$–$C_8$-arylamino, cyano, carboxyl, carboxylato of the formula $COOR^8$, where $R^8$ is a monovalent cation or a $C_1$–$C_8$-alkyl group, $C_1$–$C_8$-acyloxy, sulfinato, sulfonato of the formula $SO_3R^8$, phosphato of the formula $PO_3H_2$, $PO_3HR^8$, $PO_3R^8_2$, or tri-$C_1$–$C_6$-alkylsilyl, where two of these substituents may also be bridged, or where $R^1$ and $R^2$ or $R^4$ and $R^5$ may be joined to one another so as to form a 4–8-membered cyclic compound.

* * * * *